US011000580B2

(12) United States Patent
Lee (10) Patent No.: US 11,000,580 B2
(45) Date of Patent: May 11, 2021

(54) ROADMAP FOR CONTROLLING MALARIA

(76) Inventor: Eng Hong Lee, Guelph (CA)

( * ) Notice: Subject to any disclaimer, the term of this patent is extended or adjusted under 35 U.S.C. 154(b) by 92 days.

(21) Appl. No.: 13/997,269

(22) PCT Filed: Dec. 20, 2011

(86) PCT No.: PCT/CA2011/050788
§ 371 (c)(1),
(2), (4) Date: Jun. 23, 2013

(87) PCT Pub. No.: WO2012/088605
PCT Pub. Date: Jul. 5, 2012

(65) Prior Publication Data
US 2013/0295138 A1    Nov. 7, 2013

Related U.S. Application Data

(60) Provisional application No. 61/427,426, filed on Dec. 27, 2010.

(51) Int. Cl.
| | | |
|---|---|---|
| *A61K 39/00* | (2006.01) | |
| *A61K 39/002* | (2006.01) | |
| *A61K 39/015* | (2006.01) | |
| *A61K 49/00* | (2006.01) | |
| *A61K 39/012* | (2006.01) | |

(52) U.S. Cl.
CPC .......... *A61K 39/015* (2013.01); *A61K 39/012* (2013.01); *A61K 2039/545* (2013.01); *A61K 2039/552* (2013.01)

(58) Field of Classification Search
CPC .... A61K 39/00; A61K 39/002; A61K 39/015; A61K 49/00
USPC ...... 424/9.1, 9.2, 184.1, 234.1, 269.1, 272.1
See application file for complete search history.

(56) References Cited

U.S. PATENT DOCUMENTS

| | | |
|---|---|---|
| 6,306,385 B1 | 10/2001 | Lee |
| 2007/0087021 A1 | 4/2007 | Lee |

FOREIGN PATENT DOCUMENTS

| | | |
|---|---|---|
| CA | 1204057 | 5/1986 |
| CA | 2098773 | 12/1994 |
| WO | WO 2004/045559 | 6/2004 |

OTHER PUBLICATIONS

Frolich S., et al. "Comparison of protective immune responses to apicomplexan parasites". vol. 2012, pp. 1-11, 2012.*
Frolich, S., et al. Review Article: Comparison of Protective Immune Responses to Apicomplexan Parasites. Journal of Parasitology Research, vol. 2012, pp. 1-11.*
Roestenberg, M., et al., The New England Journal of Medicine, vol. 361, pp. 468-477, 2009.*
Epstein, J.E., et al. Journal of Infectious Diseases, vol. 196, pp. 145-154, 2007.*
Lim et al. (BMC Genomics, 13:389, pp. 1-17, 2012) ("Lim et al.").*
Gopalakrishnan et al. (Infectious Diseases, 10:303-311, 2010).*
*Falkner v. Inglis*, (448 F.3d 1357, 1365 (Fed. Cir. 2006).*
Wallach, M., Int. J. Parasitol. Oct. 1997; 27(10): 1159-67.*
Frolich et al. Journal of Parasitology Research, vol. 2012, pp. 1-11, 2012.*
Frolich et al., Parasitology, 141: 1726-1735, 2014.*
Lim et al. BMC Genomics, 13:389, pp. 1-17, 2012.*
U.S. Appl. No. 61/427,426, Lee, E-H.
U.S. Appl. No. 11/558,894, filed Apr. 19, 2007, Lee, E-H.
Lee & Al-Izzi. Avian Diseases vol. 25, pp. 503-512, 1981.
Belkaid J. et al. CD4+ CD25+ regulatory T cells control Leishmania major persistence and immunity, Nature 420, 502-507 (Dec. 5, 2002).
Menzies, D. Interpretation of Repeated Tuberculin Tests, Am. J. Respir. Crit. Care Med., vol. 159, No. 1, Jan. 1999, 15-21.
Severins, M., (Effects of heterogeneity in infection-exposure history and immunity on the dynamics of a protozoan parasite, J. R. Soc. Interface (2007) 4, 841-849).
Hoffman S.L., et al. Protection of humans against malaria by immunization with radiation-attenuated Plasmodium falciparum sporozoites, J Infect Dis. Apr. 15, 2002;185(8):1155-64.
Roestenberg M., et al. Protection against a Malaria Challenge by Sporozoite Inoculation, N Engl J Med 2009; 361:468-477 Jul. 30, 2009.
Epstein J.E., et al. Safety and Clinical Outcome of Experimental Challenge of Human Volunteers with Plasmodium falciparum-Infected Mosquitoes: An Update, The Journal of Infect The Journal of Infectious Diseases 2007; 196:145-54).
Chapman, H.D. and A.B. Kacker. (1994). Sensitivity of field isolates of Eimeria from two broiler complexes to anticoccidial drugs in the chicken. Poult. Sci. 73(9):1404-8.
Mathis, G.F. and L.R. McDougald. (1989). "Restoration of drug sensitivity on turkey farms after introduction of sensitive coccidia during controlled-exposure immunization." In: Yvové P. (Ed). Coccidia and intestinal coccidiomorphs, INRA, Paris, France, pp. 339-343.
Guilbride et al. Why Functional Pre-Erythrocytic and Bloodstage Malaria Vaccines Fail: A meta-Analysis of Fully Protective Immunizations and Novel Immunological Model PLoS ONE. May 2010 (May 2010). vol. 5, No. 5, e10685.
PCT Search Report for PCT/CA2011/050788.

(Continued)

*Primary Examiner* — Rodney P Swartz
(74) *Attorney, Agent, or Firm* — May Ming Wu (57) ABSTRACT

Embodiments of the present invention concern methods of preventing malaria in a target population of humans comprising: uniformly administering a therapeutically effective amount of a live low dose malaria vaccine to each individual within the target population on each of two or three consecutive days. The methods include using *Plasmodium* infected mosquitoes to inject *Plasmodium* into individuals through mosquito bites.

10 Claims, 4 Drawing Sheets

(56) References Cited

OTHER PUBLICATIONS

Noulin, F, Malaria modeling: In vitro stem cells vs in vivo models, World Journal of Stem Cells, Mar. 26, 2016, pp. 99-100, Baishideng Publishing Group Inc, USA.

World Health Organization, Malaria vaccines: The malaria vaccine candidate RTS,S/AS01, Accessed on Jun. 9, 2020 https://www.who.int/immunization/research/development/malaria/en/.

* cited by examiner

Figure 3: This is a sample of a data log.

Figure 4

ROADMAP FOR CONTROLLING MALARIA

CROSS REFERENCE TO RELATED APPLICATIONS

This application is a National Phase entry (under 35 USC 371) of International Patent Application Serial No. PCT/CA2011/050788 filed 20 Dec. 2011, and claims the benefit of priority of U.S. Patent Application No. 61/427,426 filed on Dec. 27, 2010. All documents cited in this application are hereby incorporated by reference in their entirety.

TECHNICAL FIELD

The present invention is directed to vaccines and methods of protecting a target population of humans against malaria.

BACKGROUND OF THE INVENTION

Protozoan diseases are endemic in many populations in the world. In chicken, the protozoan *Eimeria* causes the disease coccidiosis, which is endemic in poultry flocks raised in commercial barns throughout the world, causing morbidity and mortality where it is not well controlled. In humans, the protozoan *Plasmodium*, which causes malaria, is endemic in certain parts of the world and is a major cause of morbidity to all victims and mortality in some victims in those regions, as effective means of control have not yet been devised, and as prevailing medication is losing its effectiveness.

Coccidiosis is a very common disease of poultry, caused by several species of *Eimeria*, with *E. tenella*, *E. acervulina* and *E. maxima* being three of the most prevalent species. Species of *Eimeria* that cause coccidiosis in chickens include *E. acervulina*, *E. brunetti*, *E. maxima*, *E. mitis*, *E. mivati*, *E. necatrix*, and *E. tenella*. Presently, poultry flocks are protected against coccidiosis by immunization in breeders or parental flocks and by the use of anti-coccidial chemotherapeutic agents in broiler chickens. The study and treatment of coccidiosis is a useful model for other diseases having similar characteristics, such as malaria.

Ionophores of demonstrated commercial use in the control of coccidiosis include lasalocid, salinomycin, monensin, and narasin.

There are reports of resistant strains of *Eimeria* developing in the field as a result of the use of anti-coccidials.

Another method of controlling chronic infections is the use of immunization.

Live vaccines generally comprise live attenuated or non-attenuated strains of the causative organism, the causative organism being capable of causing a mild form of the disease.

There have been attempts to overcome the drawbacks of using either immunization or chemotherapy alone. For example, my U.S. Pat. No. 6,306,385 claims such a combination of immunization and chemotherapy for treating coccidiosis.

As noted above, malaria, caused by parasites of the genus *Plasmodium*, goes through multiple stages during its life cycle. There are four types of human malaria: *Plasmodium falciparum*, *Plasmodium vivax*, *Plasmodium malariae*, and *Plasmodium ovale*. *Plasmodium falciparum* and *Plasmodium vivax* are the most common. *Plasmodium falciparum* is the most pathogenic. In recent years, some human cases of malaria have also occurred with *Plasmodium knowlesi*—a monkey malaria that occurs in certain forested areas of South-East Asia. It has been estimated that worldwide two billion people are at risk of developing the disease and up to 500 million cases of malaria occur each year. The disease results in the death of 1 to 2 million people annually, mainly children under 5 years of age as some are not fully immunocompetent, but also a significant number of pregnant women who are immunocompromised by their condition. Generally, malaria is controlled by attempts to control the mosquitoes, which are the vector for transmittal of the disease from one human to another and through the use of anti-malarial drugs, such as various quinine derivatives. Anti-malarial drugs include quinine and related agents, chloroquine, amodiaquine, pyrimethamine, proguanil, sulfonamides, mefloquine, atovaquone, primaquine, halofantrine, doxycycline, clindamycin, and artemisinin and derivatives, and various combinations thereof. The risk with the use of such anti-malarial drugs is that the *Plasmodium* may eventually become resistant to the effects of the drug. Malaria vaccines comprising isolated surface antigens or the pre-erythrocytic stage of asexual blood-stage are presently under development using antigens identified with variant stages of the *Plasmodium*. Similarly, malaria vaccines comprising irradiated (attenuated) *Plasmodium* are also under development. Such vaccines may confer some degree of immunity but generally suffer the drawbacks of all subunit, killed or attenuated vaccines. Such vaccines do not present the full antigenic complement of the infectious organism to the host. Rather, they are limited to the antigens specific for the stage of the life cycle or to the antigens expressed during the stage of the life cycle. If the organism can break through the stage being immunized against, the host will have minimal or no immunity against other life cycles. As an example, attenuated *E. necatrix* was being used in a vaccine in the past, and this vaccine did not work well in dry regions of the world, such as the South Island of New Zealand, South Africa and Chile, for example.

Macrophages are responsible for an animal's defense against apicomplexan parasites (Lee & Al-Izzi. Avian Diseases Vol. 25, pp 503-512). Lee & Al-Izzi. showed that when macrophages were selectively killed in the peritoneal cavity of chickens previously injected with carrageenan, subsequent challenge with *Eimeria tenella* resulted in increased severity of *E. tenella* infection compared with controls. This means that macrophages play an important role in the immune protection against the first exposure to *E. tenella* and by extension, against apicomplexan parasites in general.

My U.S. patent application, published as US2007087021, describes methods of using a combination of immunization and chemotherapy to protect against malaria.

There thus remains a need for improved methods of providing effective control of malaria.

SUMMARY OF INVENTION

Effective control of coccidiosis in a target population requires repetition of a uniform administration of a low dose of live *Eimeria* vaccine to the entire target population at the same time. Otherwise those vaccinated and not yet fully protected chickens become reservoirs for those unexposed chickens.

Effective control of malaria in a target population requires repetition of a uniform administration of a low dose of live *Plasmodium* vaccine to the entire target population at the same time. Otherwise those vaccinated and not yet fully protected individuals become reservoirs for those unexposed individuals.

The present invention relates to a method of preventing malaria in a target population of humans comprising: uniformly administering a therapeutically effective amount of a live low dose malaria vaccine to each individual within the target population on each of two or three consecutive days.

The present invention relates to a method of preventing malaria in a human comprising: administering a therapeutically effective amount of a live low dose malaria vaccine to the human on each of two or three consecutive days.

The present invention relates to methods as described herein wherein the live low dose malaria vaccine contains a drug sensitive strain of *Plasmodium*.

The present invention relates to methods as described herein wherein the malaria vaccine consists of a plurality of drug sensitive *Plasmodium* infected mosquitoes in a container and the administration of the vaccine consists of allowing each individual human in the target population to be exposed to the mosquitoes in the container and receive at least five mosquito bites therefrom.

The present invention relates to methods as described herein wherein the drug to which the *Plasmodium* is sensitive is chloroquine or mefloquine.

The present invention relates to methods as described herein wherein the drug sensitive live organisms are drug sensitive due to loss of a non-chromosomal resistance gene.

BRIEF DESCRIPTION OF THE DRAWINGS

The embodiments of the present invention will now be described by reference to the following figures, in which identical reference numerals in different figures indicate identical elements and in which.

DETAILED DESCRIPTION OF THE INVENTION

*Eimeria* vaccines are an appropriate surrogate for studying *Plasmodium* vaccines for a number of reasons. *Eimeria* and *Plasmodium* are both apicomplexan protozoan parasites: they are very closely related organisms. In addition, many *Eimeria* vaccines are highly successful, have been so for many decades, and have been studied in detail. Importantly, for *Plasmodium, Eimeria* is the most closely related organism for which a successful vaccine has been developed. Moreover, *Eimeria* are species specific and do not cross infect humans, and can be safely studied in poultry. Using *Eimeria* vaccine as a surrogate, most if not all problems with *Plasmodium* vaccines can be worked upon first and solved if possible, without using human volunteers. For these reasons, many of the principles learned from observing various applications of *Eimeria* vaccines and how problems were solved can be used to develop an effective *Plasmodium* vaccine and just as importantly, an effective regime for administration of that vaccine. The dosages, timing and means for mitigation even on problems that will emerge when experiences learned from these Eimerian vaccines are being transposed to the making of malaria vaccines. All can be done much more economically and more importantly a large pool of experimental subjects that are readily available that are hatched sterile against coccidiosis. All these can be worked on with a fraction of the costs when compared to the costs of present R & D of malaria vaccines.

Both malaria and coccidiosis in commercial poultry are caused by highly successful apicomplexan parasitic diseases. Their success relies mainly on being able to live and multiply for a self limited period of time for each infection inside the same or different hosts or remain free living outside the hosts for months as the oocyst stage of coccidia. By staying inside the host for weeks or months means that the host is also the reservoir. Coccidiosis is more successful in this respect as an endemic disease than malaria because the excreted oocyst is also the infective agent, rendering technically the commercial birds playing the role of both reservoir as well as the vectors to the parasite. This dual role of reservoir-vector means that the commercial chickens and turkeys are condemned to suffer from this endemic disease, and constantly, unless there is relief coming from the use of anticoccidials added in the feed or becoming immune naturally by picking up infective oocysts from the litter or by vaccination. If non-medicated or non-vaccinated, every bird is either a healer by producing low number of oocysts to induce immunity in other birds or it is a killer to the unprotected birds if it sheds high enough numbers of oocysts. In short, your neighboring bird either heals you or kills you. There is no escape from this disease within the four walls of the commercial barn without medication or immunization, making coccidiosis truly a perfect endemic disease in commercial poultry.

In malaria, however, the role of the reservoir is played by human or animal host and the role of the vector is played by the anopheles mosquitoes. This separation of roles in the completion of the life cycle of *Plasmodium* spp has allowed the successful eradication of this disease from many countries over the years by simply interrupting the sexual stages either by killing the vectors or preventing their bites. In short, malaria is a less successful endemic disease.

Yet, there is a successful business of coccidiosis vaccines in the poultry industry. Almost all commercial chicken breeders are now vaccinated, worldwide. And, at least 3 to 4% of broiler chickens are on vaccines for coccidiosis control worldwide. Just these birds alone account for more than 2 to 3 billion doses of multivalent live vaccines being used every year and for over a decade. The increasing number of chicken egg layers and commercial turkeys that are on vaccines together potentially add millions if not billions of more doses every year.

All successful commercial coccidiosis vaccines must have the following characteristics:

1. Live vaccines: All successful and commercially available coccidiosis vaccines are live vaccines (e.g. Immucox, Coccivac). For many protozoan diseases, it is extremely difficult to control the disease through only vaccination or medication. The host relies on infection and immunity to achieve protection from further manifestations of the disease. In order to have immunity, there generally has been an infectious agent present. The difficulty with making effective vaccines for such organisms causing chronic or multiple life cycle infectious is due to the nature of the organism. Where organisms have multiple life stages, each life stage has a different antigenic complement. A vaccine which utilizes only an organism at one stage will not provide protection against other stages of the organism. This is particularly true for present dead or subunit vaccines which will not present the full antigenic complement. Thus to be most effective, a live non-attenuated vaccine is preferred.

2. Repetition of coccidiosis vaccination and/or exposure: Repeated exposure to coccidiosis (recycling or reinfection) allows the various life cycle stages to evoke immune responses from the host. Repeated exposure to coccidiosis is needed for poultry to develop full immunity because each stage of the life cycle does not cross protect one another. Although some stages are considered more essential than other stages in conferring immunity, it could very well be that the importance usually relates to pathogenicity manifested more prominently by that stage than by some others. In other word, sporozoites will only protect sporozoites and the immune response evoked has no effect on merozoites or the gametes. Moreover, subunit vaccines cannot recycle.

3. No interruption of recycling: By accidental addition of medication to the feed or by using very dry litter that is not favourable for allowing the oocysts to sporulate or become infective, there will be no immune protection as exhibited sometimes, by subsequent breaks of the disease a life cycle or two later.

4. Uniform exposure: Although one commercial coccidiosis vaccine was used before the concept of uniform exposure had been introduced (Canadian Patent No. 1,204,057, issued in 1986) all present commercial vaccines were introduced or reintroduced, all with some form of delivery system that allow some semblance of uniform exposure. Uniform exposure is made possible by the following factors:

1. Oocysts, large enough that they can be counted under the microscope and be delivered at predetermined numbers or at a recommended dose to each bird, if an effective delivery system is employed;

2. The life cycle of the Eimerian parasites are self limiting. In other word, the final number of progeny of each ingested oocyst is finite and once reached, no further progenies are produced from that ingested oocyst;

3. All hatchlings are immunologically naïve against coccidiosis because no oocysts can infect eggs or survive at incubation temperature and duration and therefore all hatchlings can start at the same point in life for their reaction to the vaccination;

4. All birds grow at the same age or rate and therefore uniformly react to the initial vaccination and closely during subsequent recycling; and 5. All vaccinated birds are disposed of en mass and oocysts left behind will take usually three generations to have enough numbers to affect the birds and by then the vaccinated hatchlings would have become immunized. And therefore, effectively disposal en mass does not leave behind infected hosts as parasite reservoirs to affect subsequent vaccinations of subsequent crops.

Many of the same principles should hold true for malaria vaccines, to the extent that the diseases are similar.

The successful control of malaria in an endemic region will depend not only on an effective vaccine, but also on an effective method of administering the vaccine to a target population.

Effective Malaria Vaccine

An effective malaria vaccine should have the following characteristics:

1. A live vaccine: necessary for both efficacy and safety. The vaccine must be live because the vaccine must be as close to 100% effective as possible, since any ineffectively vaccinated individuals will be at risk for infection and could serve as a reservoir to infect others.

Live vaccines present the best chance of success for conferring protective immunity against these infectious agents or in the form of immunity now known as infection immunity. In many case, this requires that the live vaccine induce a sub-clinical infection in the host. For many diseases which are only minimally lethal by their causative agents, this may not present a major problem if the infection caused by the vaccine should progress beyond the sub-clinical stage. For other diseases this may be unacceptable, especially if the replication is not self limiting (see above).

A live malaria vaccine is the only practical solution to controlling malaria in a large population. Subunit malaria vaccines not only are less effective and too expensive to be practical to administer to a large population compared with live malaria vaccines, but can endanger the ineffectively vaccinated and non-vaccinated remaining population. This is clearly seen even when highly effective live vaccines, supposedly given uniformly, still result in suffering from some secondary infections, some of which can be fatal: this is because some of the ineffectively vaccinated will become sick with malaria and will serve as reservoirs for mosquitoes to infect others who are ineffectively vaccinated.

2. A low dose vaccine: The organism dose in the vaccine must be low: enough to be immunogenic, but not high enough to cause disease.

It is important to use a low dose of the live protozoan organisms in a live protozoan vaccine to allow protective immunity to develop before infections become severe. High doses of a live protozoan organism will cause disease and increase morbidity and mortality in the population by spreading the protozoan disease in the population. Low doses of a live protozoan organism induce immunity and cause only subclinical disease, thereby reducing overall morbidity and mortality in the population. Low doses give one a much better chance of living through all of the protozoan cycles without problems.

3. A vaccine containing one or more drug sensitive strains of *Plasmodium*. The vaccine organism selected should be drug sensitive, so that any disease outbreaks can be mitigated by drugs. This renders the live vaccine safer for the immunocompromised or immunoincompetent (eg. infants and elderly).

Effective Methods of Administration of a Malaria Vaccine

An effective administration of malaria vaccine in an endemic region could control malaria if it has the following characteristics:

1. Simultaneous: The administration should be simultaneous, that is vaccination should occur within days to all individuals within the target population.

2. Uniform: in vaccine dose and in vaccine administration across the population. The vaccinations must be uniform, meaning as close to the whole target population as possible should receive the proper dose of vaccination, for each round of vaccination, to reduce the potential for human reservoirs of the wild type strains. Uniformity is discussed in greater detail, below.

3. Repeated: The vaccinations must be repeated, in order for individuals within the target population to develop full immunity against malaria.

Target Population

In coccidiosis, a "target population" is a population of poultry within the four walls of the barn. Because the poultry are isolated by the barn walls, infections are contained within the barn.

In malaria, a "target population" can never be as clearly defined, because neither humans nor mosquitoes can typically be contained within four walls of a building continuously and for substantially their entire lifetime. The target population in malaria is a population of humans that live within a continuous area populated by *Plasmodium* carrying mosquitoes. It is the malaria carrying mosquitoes that define the border of an endemic area, and those humans within that border are the target population. Throughout the world there are pockets of endemic areas. Each of these malarial endemic areas that are isolated from one another has a separate target population of humans within them.

Immune response to both coccidiosis and malaria is cell mediated, and seemingly there is no immune memory. Both infections appear to follow a modified cycle. Therefore, it is not unexpected that both diseases rely on infection immunity to protect the host.

Infection Immunity: Reason for a Live Vaccine

Infection immunity is said to occur where small amounts of organism remain inside the body following exposure without causing active disease in the host. Infection immunity is a phenomenon well described for *Leishmania major*, where a small number of parasites remain in the injected site for the host to remain protected (see Belkaid J. Et al. CD4+ CD25+ regulatory T cells control *Leishmania major* persistence and immunity, Nature 420, 502-507 (5 Dec. 2002)). Infection immunity is a negotiated truce. It is a host-parasite relationship. If the parasite lets the host live, the host may allow the parasite to survive within the host for the long term. Tuberculosis is another example of infection immunity. About one third of the world is tuberculin sensitive: this means that one third of the world has been exposed to tuberculosis and has either infection immunity or has the disease. Once a person tests positive for TB, one never loses the immunity (see Menzies, D. Interpretation of Repeated Tuberculin Tests, Am. J. Respir. Crit. Care Med., Volume 159, Number 1, January 1999, 15-21). It is a host's way of compromising: if an organism does not overwhelm us and cause disease, then it may be able to live inside our body somewhere without harming us. Thirty percent of our genomes are viruses. Many of our proto-onco genes are originally viruses. Malaria and coccidiosis are two diseases where infection immunity occurs between host and infectious agent.

When the host finally expels the parasite, the host becomes susceptible again or so called sterile immunity. Therefore it is no surprise that under this endemic condition, protection against coccidiosis in early commercial operations relied on the constant supply of medication, because of the unending emergence of drug resistance. The search for alternative methods of control later was spurred on by drug-resistance to all existing anticoccidials. In the development of vaccines, differences between the controls of these two diseases start to diverge. Development of malaria vaccines up until recently are primarily concerned with vaccine safety and therefore research has concentrated mainly on the development of recombinant vaccines. Because of these safety concerns and due to avoidance of live vaccines, only occasional glimpses of success have been seen such as when irradiated-sporozoites were used for challenging purposes leading to protective immunity. No such great concern hampered the development of vaccines against coccidiosis. The development started with live vaccines and became immediately successful.

It is because immunity against malaria relies on infection immunity, that a live malaria vaccine is the most likely to be successful.

There is no immune memory similar to that which works for small pox vaccination. Therefore, the so-called herd vaccination is not sufficient in coccidiosis vaccination as a control because any non-vaccinated member or vaccinated member losing its residual infection immediately becomes susceptible to re-infection. Therefore, use of genetic mutant strains, non-replicative strains or physiologically deficient strains which can only create herd vaccination cannot achieve total population vaccination. In addition, protection is short lived and repetitions of vaccination must be frequent to achieve total population vaccination.

If low dose and live organisms are also essential for malaria vaccination, perhaps, this can explain partly why subunit vaccines, which were sought after for safety reasons, have only obtained partial successes now and then.

Cocci Vaccines: Live, Low Dose and Drug Sensitive

The success of coccidiosis vaccination also leads to two or other side benefits for the control of coccidiosis. By using drug-sensitive strains in the vaccines, the field strains, which are largely drug resistant, can be temporarily displaced. Then after using the vaccine for a few flocks, the same anticoccidials can be reused again for a few flocks or until the return of the drug-resistant strains (Mathis, G. F. and L. R. McDougald. (1989). "Restoration of drug sensitivity on turkey farms after introduction of sensitive coccidia during controlled-exposure immunization." In: Yvové P. (Ed). Coccidia and intestinal coccidiomorphs, INRA, Paris, France. pp. 339-343. Chapman, H. D. and A. B. Kacker. (1994). Sensitivity of field isolates of Eimeria from two broiler complexes to anticoccidial drugs in the chicken. Poult. Sci. 73(9):1404-8.)". This rotating use of vaccination and medication was further modified (U.S. Pat. No. 6,306,385, issued to Lee in 2001) to combine vaccination and medication in the same flock.

In summary, the primary success of coccidiosis vaccination appears to rely on total population vaccination and achieving endemic autogenous environment with the vaccine strains. To achieve total population vaccination, the strains must be able to compete at least at the initial vaccination with the field strains or wild-type strains, and which are preferably only mildly pathogenic. Vaccine, when repeatedly used, will generate autogenous conditions. The combination of vaccination and medication, will reduce pain and suffering from the use of live vaccines. The vaccine strains must therefore be sensitive or partially sensitive to medication in order to use this combination method.

Uniformity: Uniform Dose and Exposure to Entire Target Population

Uniform administration of protozoan vaccine, meaning administration of a therapeutically effective amount of vaccine to each individual in a target population, is key to controlling an endemic protozoan disease. If the target population is not uniformly vaccinated, those individuals in the population who are not vaccinated can be a reservoir for the protozoa, which diminishes control of the disease, since those individuals will carry the protozoa that will eventually infect others who are not vaccinated or immunized in the population.

Malaria and cocci are endemic diseases and the hosts are also reservoirs themselves until they become immunized. As a result, both malaria and cocci are diseases where the immune status of individuals within a target population has a substantial impact on the immunity of other individuals within that population. Malaria and Cocci have even more impact than diseases transmitted by contact, because those diseases are controllable by isolation practices. Herd immunization does not work with malaria because mosquitoes transfer it: isolation from the mosquito is often not possible. Therefore understanding and controlling the population dynamics of malaria are important to the control of malaria.

The population dynamics of malaria are important but are largely ignored by malarial researchers in general. Cocci researchers study isolated populations in barns besides working with effective coccidiosis vaccines. Malaria researchers do not have the advantage of seeing the whole population inside the four walls of a barn, nor are they working with vaccines that work consistently.

The dynamics of coccidiosis disease in poultry populations has been studied in a mathematical/simulation model by Severins, M., et al. (Effects of heterogeneity in infection-exposure history and immunity on the dynamics of a protozoan parasite, *J. R. Soc. Interface* (2007) 4, 841-849). In Severins, from FIG. 1b-d, (FIG. 1b is reproduced as FIG. 4 in this application) it can be seen that where 80% of the population is vaccinated at low levels, total population immunity was achieved much more quickly compared with populations where only 10% or less of the population were vaccinated. Though it is hard to achieve 100% vaccination levels, as can be seen from this model, the population with the closest percentage to 100% vaccination, was the fastest at achieving 100% immunity in the population. Uniformity of vaccination, and at low doses, are clearly important aspects of quickly achieving total population immunity for coccidiosis, minimizing the time needed to achieve immunity, and thereby decreasing the population's exposure to the disease. Indeed, it is important for other diseases as well, such as malaria.

Figure 4:
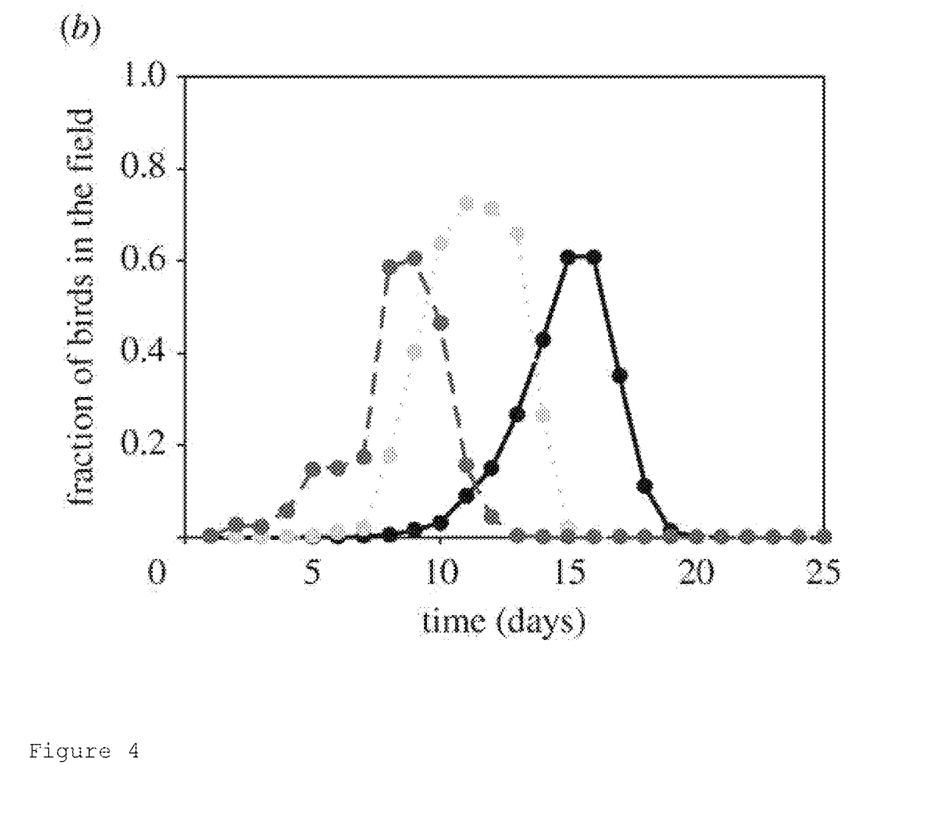
FIG. 4 is a reproduction of a graph from Severins, M., et al. (Effects of heterogeneity in infection-exposure history and immunity on the dynamics of a protozoan parasite, J. R. Soc. Interface (2007) 4, 841-849) showing that immunity develops faster with uniform administration (80%=broken line), compared with non-uniform administration (10%=dotted line, 1%=solid line).

In FIG. 4 (FIG. 1b of Severins et al.,) the first cycle (broken line) of oocysts shed by *E. acervulina* started earlier (5 days instead of 7 days for the vaccine). It was not present when the contamination or vaccination level was too low or with just 0.01 or 1% (solid line). Similarly, we have observed a first cycling of oocysts with use of Immucox vaccines during the time line for a first cycle, but not with other cocci vaccines.

The importance of uniformity can be observed by comparing the results of using the Coccivac coccidiosis vaccine and Immucox coccidiosis vaccine. Coccivac works very well against coccidiosis, however a slight disuniformity in the vaccine dosing is sufficient to invite secondary infection with necrotic enteritis (see Table 3, below).

Table 3 shows that mortality with Coccivac is much higher compared with Immucox at one farm.

TABLE 3

Mortality Rate of Consecutive Crops of Chicken Broilers on Coccivac versus IMMUCOX in an Ontario Farm (BE Farm)[a]

| Vaccine | Placement Date | Age (Days) | # Placed | Total Dead Birds | Mortality Rate % |
|---|---|---|---|---|---|
| Coccivac | May 22, 2008 | 42 | 8,160 | 573 | 7.0* |
| | May 22, 2008 | 42 | 8,160 | 263 | 3.2 |
| | May 22, 2008 | 40 | 18,360 | 590 | 3.2 |
| | Jul. 24, 2008 | 42 | 7,650 | 852 | 11.1* |
| | Jul. 24, 2008 | 40 | 7,620 | 766 | 10.1* |
| | Jul. 24, 2008 | 40 | 17,136 | 774 | 4.5 |
| IMMUCOX | Sep. 25, 2008 | 40 | 7,446 | 435 | 5.8 |
| | Sep. 25, 2008 | 42 | 7,446 | 290 | 3.9 |
| | Sep. 25, 2008** | | | | |
| | Dec. 04, 2008 | 40 | 7,344 | 385 | 5.2 |
| | Dec. 04, 2008 | 40 | 14,790 | 474 | 3.2 |
| | Dec. 04, 2008 | 40 | 7,344 | 284 | 3.9 |
| | Jan. 30, 2009 | 40 | 13,770 | 598 | 4.3 |
| | Jan. 30, 2009 | 41 | 6,936 | 321 | 4.6 |
| | Jan. 30, 2009 | 41 | 6,834 | 269 | 3.9 |
| | Mar. 23, 2009 | 38 | 16,116 | 403 | 4.6 |
| | Mar. 23, 2009 | 39 | 8,058 | 270 | 3.4 |
| | Mar. 23, 2009 | 39 | 8,058 | 283 | 3.5 |

*Necrotic Enteritis (NE)
**Summer heat problem
[a]No sign of NE to date (September 2010)

Figure 3:
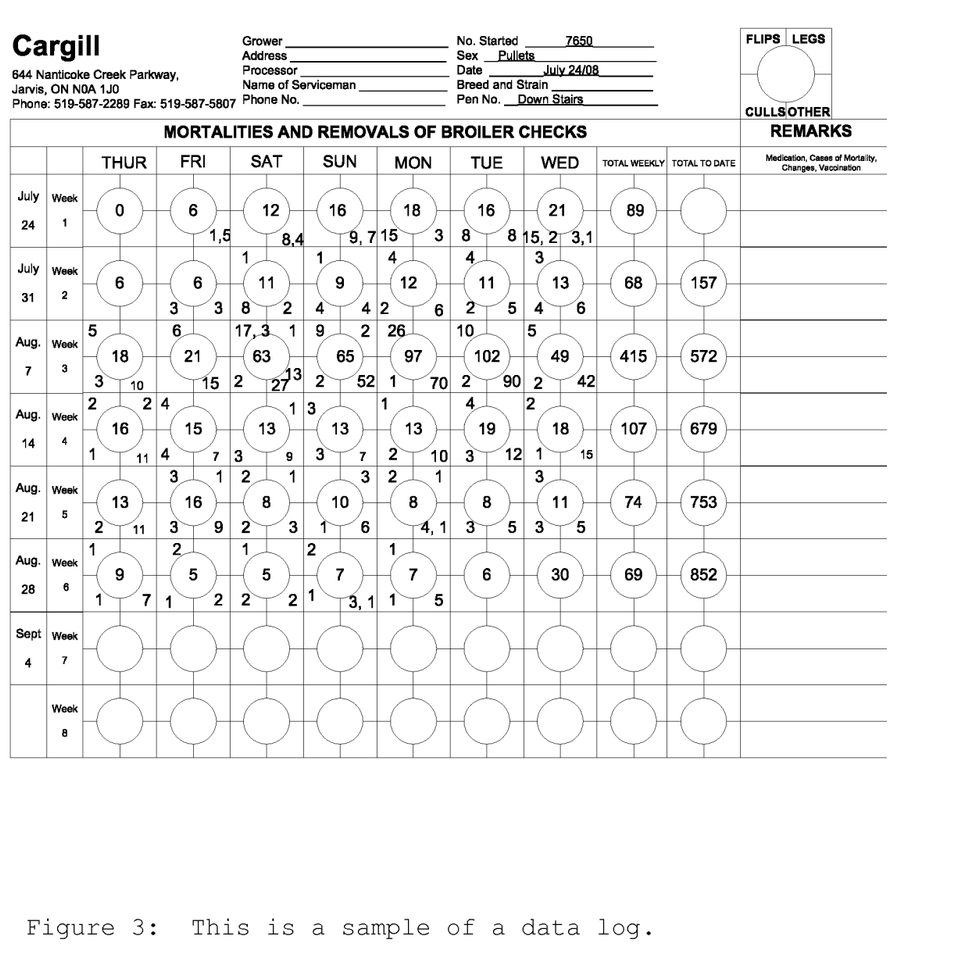
FIG. 3 are mortality results from the Bruce Evon Farm in Harriston Ontario with use of Coccivac.

The mortality rates with Coccivac can be quite high, as can also be seen from the mortality results in FIG. 3. These results are from the Bruce Evon Farm in Harriston Ontario.

With Immucox, because 75% of the birds are exposed to coccidia in the first cycle, it is easy for the exposed birds to spread cocci to the remaining 25% of the birds in the second cycle. Therefore, about 99% of the flock is exposed to cocci after the second cycle when vaccinated once in the first cycle with Immucox.

Necrotic enteritis occurs when there is too much cocci in some birds and none in others: a possible result of some disuniformity in the coccidiosis vaccine itself and/or in the administration of the vaccine. Necrotic enteritis is a secondary infection caused by *Clostridium perfringens* that arises due to the intestinal lesions caused by cocci.

With Coccivac, the initial slight disuniformity in cocci dosing, which seeds all future cycles, perpetuates itself and worsens with each subsequent cycle. Too few birds exposed to cocci in early cycles become reservoirs that can infect too many unexposed birds in later cycles. Secondary infection with clostridia is a result of the uneven harboring of organisms: lack of uniform exposure across the poultry population to cocci vaccine organisms.

With Immucox coccidiosis vaccines you can raise both chickens and turkeys in consecutive crops of production with no outbreaks of Necrotic Enteritis (NE). A similar claim cannot be made with other coccidiosis vaccines to date.

All coccidiosis vaccines are effective in controlling coccidiosis. However, some are not uniform in either production or delivery, resulting in secondary infections from time to time. Uniformity is critical to vaccine safety.

With the Immucox gel droplet system, the gel solution is designed to suspend the oocysts, and even species suspension is achieved by shaking vigorously for a short period, such as one minute or less during mixing. The uniform suspension can be maintained for hours without further agitation. Thus, Immucox gel droplet system (Gel-Spray) vaccines can be presented uniformly with each droplet of vaccine consumed as well as being presented in its multivalent nature.

Because of these two obvious differences, Immucox gel droplet system vaccines can achieve NE free production crop after crop. However, the water suspended vaccines cannot achieve NE free production in consecutive crops. Instead, use of the water suspended vaccines results in Necrotic Enteritis and suffering of fatal consequences or even heavy losses in antibiotic-free (ABF) birds where treatments are not allowed, as one treatment with antibiotics will cause the loss of the crop's ABF status.

It is important for as many individuals within the target population as possible to have exposure to the organism at first instance and at a low dose. One must target the whole population for vaccination; otherwise uneven exposure will result in problems for the unexposed. This is true even if one uses agents that are highly effective because the vaccine will only protect you if you are vaccinated. Therefore, say a subunit vaccine may protect 50% of a population, but what happens to the other 50% of the population? Those who cannot afford an expensive subunit vaccine will be at risk. The vaccinated will have mild infection and will be a temporary reservoir, which may infect the unvaccinated. Any small increased risk of malaria in the population may result in a large increase in morbidity and mortality due to secondary infections: this is illustrated by the cocci/necrotic enteritis example. With malaria, secondary infections can also occur, such as with tuberculosis (TB) or with influenza (flu). A small portion of the population will still suffer the consequences if the first vaccination is not thorough enough. Therefore, partial protection is no protection at all.

In areas of endemic malaria, everyone becomes sick with malaria every year. Each person is ill with malaria 2 to 3 times per year. Each bout of malaria will cause at least 4 to 5 days of absence from work if not more. A bad bout of malaria can result in 10 to 20 bedridden days in some cases.

Uniformity within a Range

With cocci, even when one gives a fixed amount of good vaccine with a good delivery system, the amount that each bird receives is slightly different: it is impossible to give each bird exactly the same amount. However, it is not necessary to achieve a perfect degree of uniform vaccine delivery, because the immune system of the average bird can handle a range of oocysts within the same magnitude. Slight variations in vaccine doses still works because of the recycling of cocci helps to achieve the protective level across the population. No single individual is spared of the infection. The uniformity of the vaccine does not have to be absolutely uniform: the host can work within a certain range that is immune inducing but not disease causing, i.e. not overwhelming the body with organisms.

Administration: Simultaneously

Vaccination of the entire population at the same time is also important. In order for the wild strain protozoa to be replaced by a drug sensitive protozoa in an entire endemic territory, the wild strain must be wiped out in one fell swoop. That is, the entire population must undergo vaccination at the same time, at least within days. Much the way flu clinics are run during flu season or a pandemic, clinics to mass vaccinate against malaria could also be held to vaccinate everyone at roughly the same time. In controlling coccidia, an entire flock of poultry in a barn is vaccinated together at the same time, and this has been found to be effective. The wild strain of coccidia can be and has been effectively replaced by a drug sensitive strain in the barn. A target population could continue to recycle a sensitive strain of *Plasmodium*, much like coccidiosis in chickens, but within the invisible four walls until this strain of *Plasmodium* spp. is self perpetuating. Ideally, the exposure of a given target population to the live malaria vaccine should be within a day or two.

The entire target population must be vaccinated at the same time in order to protect everyone from the protozoan disease. Any individuals who are not vaccinated can be reservoirs for the protozoan disease, preventing control of the disease throughout the population. Disease outbreaks will spread from those individuals who are not immunized. In part, this is because the wild strain protozoa will live and reproduce in those individuals, not the drug sensitive strain, causing spread of a strain that is resistant to drugs. If the entire population is vaccinated, the wild strain will be replaced by the drug sensitive strain after one or two completions of the vaccination cycle.

Administration: Repeated

Multiple exposures to live protozoan organisms are necessary to develop immunity. It takes many doses of live protozoan organism to teach the body to recognize and kill the protozoa. With cocci, a second cycle is needed to achieve immunity in 99% of the population, to avoid endangering a large percentage of the population.

Therefore, a single vaccination against malaria will not be sufficient to control the disease. Rather, several vaccinations in each individual will be required to achieve full immunity in the population. Furthermore, it will be difficult to vaccinate an entire human population in an endemic area, but over time, the wild strain will begin to be replaced by the drug sensitive strain as more people see the value of the vaccination and more people are vaccinated. In coccidia, cycling of the parasite is a necessary part of developing immunity against the parasite. A single vaccination can be effective in controlling coccidia in chicken because the chicken are reseeded with coccidia which they pick up from their feces on the barn floor for recycling. However, with malaria, humans will not have such a source for receiving subsequent doses of malaria, or not as easily. Therefore, it is wise to work with a drug-sensitive strain so that the drug to which the strain is sensitive can be used to mitigate the vaccination, if needed. It helps if mildly infective strains can be identified and used.

Other Methods of Controlling Malaria

*Plasmodium* because of its multiple state life cycle is difficult to control, especially through immunization. In the past, most of the infections have been controlled either by control of the transmission vector, the mosquito for malaria, or by antibiotics effective against the organism itself. In many cases, the organisms have mutated to be resistant to many of the control agents.

With cocci, there is a single host. With malaria there are two hosts: mosquito and humans. With malaria, it is possible to break the cycle by controlling one host (exterminating mosquitoes or draining swamps for example). Whereas with cocci it is not possible: cocci is endemic within barns, there is a single host, poultry, and the poultry are confined within four walls: there is no place for them to run. Therefore cocci are more hazardous to their host in comparison with malaria which involves two hosts to complete the cycle. The life cycle of malaria is more intermittently interrupted, unlike the chicken walled in and constantly exposed and with their habit of pecking the litter and thereby causing their own infection. The pecking of the litter also leads to the success of coccidiosis vaccines, which allows the birds to consume vaccine leading to immunity. With *Plasmodium*, repeated bites are needed to reach full protective immunity.

Route of Administration of Malaria Vaccine

The vaccination against malaria must be done using mosquitoes because introduction of sporozoites by any other means will be too time consuming, too expensive and impractical. Furthermore, even the best vaccine in development has only a 90% effectiveness rate (See Hoffman S. L., et al. Protection of humans against malaria by immunization with radiation-attenuated *Plasmodium falciparum* sporozoites, J Infect Dis. 2002 Apr. 15; 185(8):1155-64. Epub 2002 Apr. 1). The art of live vaccination of people with malaria using malaria infected mosquitoes is well known. Vaccination using mosquitoes to deliver whole live non-attenuated *Plasmodium* to humans has been tested and achieved 100% vaccination in one small experiment (see Roestenberg M., et al. Protection against a Malaria Challenge by Sporozoite Inoculation, N Engl J Med 2009; 361:468-477 Jul. 30, 2009). One can culture and maintain *Plasmodium*-infected mosquitoes in a container by feeding them a *Plasmodium*-infected blood meal using, for example, a glass membrane feeder. One needs to be exposed to the bites of at least five *Plasmodium*-infected mosquitoes (5 bites) to get an effective dose to reach protective immunity 100% of the time. (See Epstein J. E., et al. Safety and Clinical Outcome of Experimental Challenge of Human Volunteers with *Plasmodium falciparum*-Infected Mosquitoes: An Update, The Journal of Infectious Diseases 2007; 196:145-54)

The following is provided in Roestenberg, cited above, at pages 469 to 470: . . . While receiving chloroquine, subjects in the vaccine group were exposed on three occasions at monthly intervals to bites of 12 to 15 mosquitoes that had been infected with *P. falciparum*, for a total exposure of bites from 36 to 45 infected mosquitoes per subject. Control subjects received bites from an equal number of uninfected mosquitoes on the same occasions. *Anopheles stephensi* mosquitoes were reared according to standard procedures at our insectary. Infected mosquitoes were obtained by feeding on gametocytes of NF54, a chloroquine-sensitive strain of *P. falciparum*, as described previously. NF54 is genetically homogeneous but has not been formally cloned. Only the technicians who prepared the mosquitoes were aware of their infectivity status, and these staff members had no clinical involvement with the subjects or the investigators. Blood-engorged mosquitoes were dissected to confirm the presence of sporozoites. If necessary, feeding sessions were repeated until precisely the predefined number of infected mosquitoes had fed . . .

The following is provided in Epstein, cited above, at page 146, column 2: Challenge procedures. For the experimental challenge, volunteers were exposed to the bites of 5 *A. stephensi* mosquitoes verified to have taken a blood meal and to be infected with *P. falciparum* (NF54 strain) sporozoites with a gland grade of 2+ (11-100 sporozoites) or greater by postfeeding microscopic examination of salivary glands, as described elsewhere . . .

Safety

Researchers already know how to vaccinate with live *Plasmodium* in humans by using mosquitoes. However, the problem now is knowing how to make such a vaccine safe. The ideas in this patent application explain how to make this vaccine safe for use in humans.

Drug Sensitive Strain

The live protozoan organisms ideally should be chosen from drug sensitive strains. This increases the safety of the vaccine for the population, because if a low dose of live protozoan vaccine is high enough to cause disease in an immunocompromised, a very young or a very old individual in the population, that individual can effectively be treated with anti-protozoan drugs, because those vaccine strains are drug sensitive. The choice of drug sensitive strains allows health care workers a chance to mitigate any adverse effects of the live vaccine, such as inducement of disease in susceptible individuals, by preserving the effectiveness of anti-protozoan drugs.

The combination of vaccination and medication, described in my U.S. Pat. No. 6,306,385, is equally applicable to Malaria. Use of drug sensitive strains will salvage the use of drugs that have acquired resistance in the field. Autogenous strains with particular traits can be grown and used in the vaccine. In particular, malarial organisms with non-chromosomal resistant traits can be selected for absence of resistance. For example, chloroquine resistance is a non-chromosomal resistant trait. Malarial organisms can spontaneously loose chloroquine resistance: these organisms should be chosen for vaccine production. In this manner, if a person vaccinated develops malaria, they can be treated with chloroquine.

With coccidia, Vetech Laboratories Inc. has used the same strain for 25 years.

Of all vaccines on the market for cocci (4 or 5), all are highly effective in the control of coccidiosis, even though they are isolated in different geographic locations throughout the world and one can use all of those vaccines all over the world. Immucox has been used and is effective in over 30 countries all over the world. Similarly, a *Plasmodium* strain, particularly a drug sensitive strain, could also be isolated in one location and used effectively in a malaria vaccine throughout the world.

Drug Sensitive Strains in the Vaccination/Medication Method

Vaccination and medication can be used in combination to optimize prevention and/or treatment of disease. After an infectious organism is administered to the host by way of vaccination, the host is left to be exposed to the entire antigenic complement of the organism to enable it to develop the full immunological response to the infective organism before the commencement of chemotherapy. Ideally, the period of time between administration of the infective organism and the commencement of chemotherapy would correspond to about one life cycle of infectious cycle of the infective organism. This will enable the host to be exposed to the full antigenic complement of the infective organism, particularly for those infective organisms which go through various stages in the life cycle.

In addition, the vaccine may also contain organisms which have been genetically engineered to optimize the protection of the host to the organisms to which the host would be exposed in the natural environment. For example, if a particularly virulent strain of the organism is present in the natural environment, the organism for the vaccine could be engineered to utilize a less virulent species or strain of the organism, the less virulent species or strain of the organism in the vaccine also being capable of expressing antigens on its surface which cross-react with, or are specific for the more virulent strain found in the natural environment. This would optimize the protection of the host to the strain found in the natural environment while minimizing the effects of the vaccine on the host. One example of a genetically engineered organism is the recombinant coccidian described in my Canadian Patent No. 2,098,773, issued Sep. 21, 1999.

Many of the organisms which cause chronic infection have common characteristics such as minimal cross species protection as well as minimal cross strain protection. Thus immunizing against a particular species or even a strain of a particular species, does not necessarily confer immunity to infections caused by other species of the organism or other strains of the species of the organism.

To be most effective, the vaccine is administered replicating the natural route of infection by the organism in the normal cause. In this way, the host develops the proper immunity to the infectious agent.

All documents referred to in this application are hereby incorporated by reference in their entirety.

The following examples are utilized to illustrate preferred embodiments of the present invention but are not to be construed as limiting the scope of the invention to the specific examples.

Example 1

Exploratory Test on Early Protective Immunity of Chickens by Repeated Gavages of a Known Level of a Commercial Vaccine Twenty 11 day old chick were inoculated by gavage with 100 µL of a coccidiosis vaccine (Immucox) reconstituted at 1,000 doses into 250 ml of gel droplets mixture. The same was repeated the next day and again the day after, At 7 days post Day 1 vaccination, one group of 10 birds was challenged with $2.5 \times 10^5$ oocysts of *E. acervulina* $5 \times 10^4$ oocysts of *E. tenella* and the remaining 10 birds with $3.75 \times 10^5$ oocysts of *E. acervulina* and $7.5 \times 10^4$ oocysts of *E. tenella*. None of the challenged birds died and all lesions were scored mostly between 2 and 3.

TABLE 4

These results showed that early protective immunity can be achieved as early as 7 days of age with a scheme of low dose and repeated inoculations of coccidial oocysts.
Table 4. Exploratory test on early immunity of chickens against coccidiosis by repeated gavages of a known level of a commercial vaccine

| | | | Lesion scores | |
|---|---|---|---|---|
| Group | Challenged | Mortality (%) | Duodenal | Cecal |
| 1 | $2.5 \times 10^5$ *E. acervulina* $5 \times 10^4$ *E. tenella* | 0/10 (0) | 2.19 | 2.59 |
| 2 | $3.75 \times 10^5$ *E. acervulina* $7.5 \times 10^4$ *E. tenella* | 0/10 (0) | 2.2 | 2.78 |

Example 2

One hundred and forty chicks from Hendrix Poultry, Cambridge Ontario were used for these tests. The chicks were divided into 7 groups of 20 birds and were treated in 2 different ways: Treatment 1 consisted of 2×20 chicks with one group were gavaged with 100 µL of chicken coccidiosis vaccine (Immucox) diluted as previously described in Example 1 and gavages were carried out similarly. The second group of 20 were used as non-vaccinated controls and later as challenged controls.

Treatment 2 consisted of 5×20 chicks with 3 groups gavaged with 50 µL of vaccine diluted as described above. Gavages were repeated on only two groups at 2 days of age and repeated on only 1 group on Day 3, thus ending with 1 group with 1 gavage, 1 with 2 gavages and the third with 3 gavages.

All challenged birds were gavaged with $2.5 \times 10^5$ oocysts of *E. acervulina* and $5 \times 10^4$ oocysts of *E. tenella*. Results are shown in Table 5.

TABLE 5

Effect of vaccination by repeated inoculation of young chicks with two different levels of a commercial coccidiosis vaccine (Immucox ®)

| | | | Lesion Score | |
|---|---|---|---|---|
| Vaccination | Challenged* On | Mortality (%) | Duodenal | Cecal |
| Treatment 1: | | | | |
| Controls Challenged | Day 7 | 10/18 (55.5) | $3.28^a$ | $3.50^a$ |
| 3 Gavages | Day 7 | 0/18 (0) | $2.17^b$ | $2.62^b$ |
| Treatment 2: | | | | |
| Controls nonvaccinated unchallenged | | 0/20 (0) | 0 | 0 |
| Controls nonvaccinated challenged | Day 9 | 10/21 (47.6) | $3.04^a$ | $3.55^a$ |
| 1 gavage | Day 9 | 1/20 (5) | $2.33^b$ | $2.11^b$ |
| 2 gavages | Day 9 | 3/20 (15) | $2.28^b$ | $2.40^b$ |
| 3 gavages | Day 9 | 2/20 (10) | $2.02^b$ | $2.32^b$ |

*Such challenged birds were inoculated with $2.5 \times 10^5$ oocysts of *E. acervulina* and $5 \times 10^5$ oocysts of *E. tenella*.
$^a$= probability level of $P < 0.05$ significance of being statistically different
$^b$= probability level of $P < 0.05$ significance of being statistically different

Therapeutically Effective Amount

The Day 7 challenges (Treatment 1) appeared to show that these birds were better protected than those challenged 2 days later (Treatment 2) from mortality of 0% versus 10%. These results suggest perhaps there is a minimum dose required if early protective immunity by repeated inoculations is desired.

The difference in dosing between the Treatment 1 groups (100 µL of vaccine) versus the Treatment 2 groups (50 µL of vaccine) shows the importance of using a therapeutically effective amount or dose. The dose of 50 µL of Immucox given at least once is typically fully protective after two cycles if the birds have exposure to cocci in a second cycle by picking it up from the barn floor, but this does not provide early protective immunity. From these experiments, it is clear that 50 µL is a subtherapeutic dose for achieving early protective immunity. Administration of such lesser amount will result in mortality in some members of the population if challenged early. As can be seen from the results of early challenge, the half dose (50 µL) resulted in some degree of mortality in all those groups, whereas the full dose (100 µL) did not. Treatment 1 provided a therapeutically effective amount for achieving early protective immunity, whereas Treatment 2 did not. From this, it appears that the therapeutically effective amount for achieving early protective immunity is twice the minimum amount for achieving full protective immunity where the exposure is once per cycle for two cycles.

Early protective immunity can be achieved by day 7, and therefore must be cell mediated immunity, since humoral immunity normally does not develop until 13 days post first exposure or later.

Examples 1 and 2

Multiple Vaccinations within the First Cycle

For a live vaccine to be able to control coccidiosis, the period of time before protective immunity takes hold, has to be shorter than the first appearance of disease after the parasites gain entry into the host. Otherwise, the vaccine itself is hazardous if the vaccine strains are virulent or unattenuated field strains. Conversely, all live vaccines of parasites capable of evoking protective immunity before the emergence of disease, should provide similar immunological protection against the same constituent species or strains of parasites in the vaccines.

This principle is likely correct as evidenced by the fact that all commercial live coccidial vaccines work, including vaccines with field strains that were shown to be highly virulent or highly drug resistant to most anticoccidials.

In poultry, the number days required for protective immunity to emerge is the same or less than the number of days of the incubation period of disease. Poultry require about 7 to 9 days to complete a first cycling of coccidiosis, which will provide at least partial immunity, and coccidiosis does not appear as a disease until day 13 for turkeys, and day 14 for chicken. Therefore, poultry vaccinated against coccidiosis at day 1 are protected from challenges otherwise lethal to non-vaccinated birds by about day 7 to day 9, well before the appearance of disease, around day 13 or day 14. Among the apicomplexan parasites, none are as lethal as coccidiosis. If the time for emergence of protective immunity is shorter than the incubation period of the disease, early immunization will be successful, no matter how virulent the organism.

Likely, the same principle can be extended not only to other Apicomplexan parasites but also to all diseases which exhibit the phenomenon of "infection immunity".

For example, malaria and *Leishmania major*.

The Examples show the second dose of coccidiosis vaccine can be given before the end of the first cycle resulting from the first dose of vaccine. This means that the second cycle, necessary to development of full immunity in poultry, can begin earlier than the end of the first cycle. This speeds up the development of immunity in the animal. This concept was tested in broiler chicken, as described in the Examples.

The implication for malaria is apparent. It may be possible to speed up the time to full immunity by starting each revaccination before the end of the first cycle.

Figure 1:
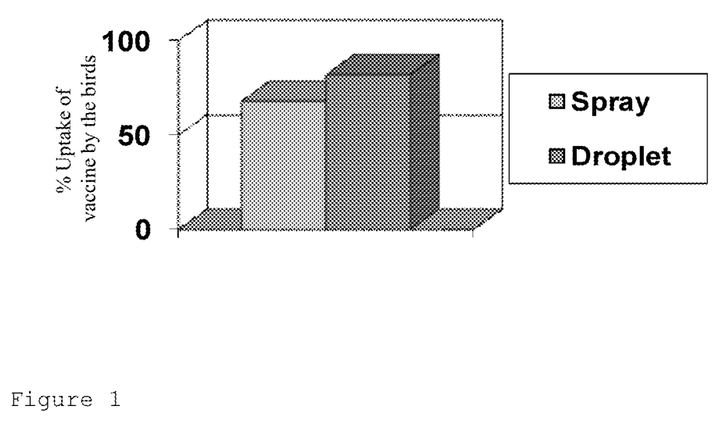
FIG. 1 is a graph showing that the uptake of vaccine is higher with Immucox Gel-Spray (Droplet, right bar graph), compared with Coccivac (Spray, left bar graph).
Figure 2:
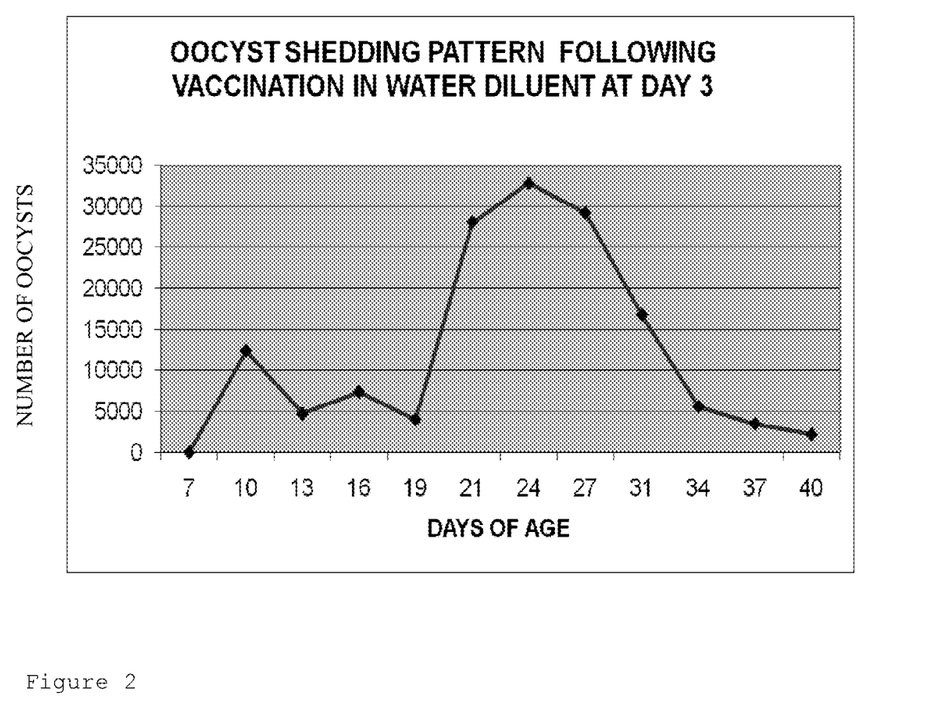
FIG. 2 is a graph showing turkey oocyst shedding pattern following vaccination with water diluent at day 3.

For example, in malaria, 8 days plus 48 hours (10 days) must pass between infection and emergence of the disease. The liver stage, which is the initial asymptomatic stage, is 8 to 27 days long. Once the malarial organisms break out of the red cells, at that stage one sees symptoms of the disease. From the Roestenberg M. et al 2009 NEJM article (see above), the immunization phase for a live malaria vaccine is about 9 to 10 days long (see FIG. 2A of that article), with a reduction in parasite number beginning around day 8. Therefore, some level of immunity is reached by about day 8.

How does infection immunity work in malaria and why do some people have immunity and others do not? The answer may be that those with infection immunity, i.e. those who retain small amounts of *Plasmodium* in their bodies, after low dose repeated infection like the Eimerian vaccines, develops the immunity. Whereas those who lose immunity, may have gotten rid of all *Plasmodium* organisms, and as a result are unprotected (lack of infection immunity).

7 days is good enough because the equivalent of $2^{nd}$ schizont stage of malaria takes a minimum of 7 days in comparison to the 5 days in coccidia. After vaccination, usually a significant cocci challenge does not occur until at least 14 days or when complete immunity has been achieved.

Having thus described the invention, what is claimed as new and secured by Letters Patent is:

1. A method of administering a malaria composition to a target population of humans comprising: administering said malaria composition to each human in the target population, wherein the malaria composition consists of at least five drug sensitive *Plasmodium* infected mosquitoes in a container, the malaria composition being administered by allowing each individual human in the target population to be exposed to the *Plasmodium* infected mosquitoes and receive at least five mosquito bites therefrom, wherein the malaria composition is administered to each individual within the target population on each of two consecutive days, wherein the drug sensitive live organisms are drug sensitive due to loss of a non-chromosomal resistance gene.

2. A method of administering a malaria composition to a human comprising: administering said malaria composition to the human, wherein the malaria composition consists of at least five drug sensitive *Plasmodium* infected mosquitoes in a container, the malaria composition being administered by allowing the human to be exposed to the *Plasmodium* infected mosquitoes and receive at least five mosquito bites therefrom, wherein the malaria composition is administered to the human on each of two consecutive days, wherein the drug sensitive live organisms are drug sensitive due to loss of a non-chromosomal resistance gene.

3. The method of claim 2 further comprising administering the malaria composition to the human on a third consecutive day.

4. A method of administering a malaria composition to a target population of humans comprising: administering said malaria composition to each human in the target population, wherein the malaria composition consists of at least five drug sensitive *Plasmodium* infected mosquitoes in a container, the malaria composition being administered by allowing each individual human in the target population to be exposed to the *Plasmodium* infected mosquitoes and receive at least five mosquito bites therefrom, wherein the malaria composition is administered to each individual within the target population on each of three consecutive days, wherein the drug sensitive live organisms are drug sensitive due to loss of a non-chromosomal resistance gene.

5. The method of claim 1 wherein the at least five mosquito bites is five mosquito bites.

6. The method of claim 1 wherein the at least five mosquito bites is twelve to fifteen mosquito bites.

7. The method of claim 2 wherein the at least five mosquito bites is five mosquito bites.

8. The method of claim 2 wherein the at least five mosquito bites is twelve to fifteen mosquito bites.

9. The method of claim 4 wherein the at least five mosquito bites is five mosquito bites.

10. The method of claim 4 wherein the at least five mosquito bites is twelve to fifteen mosquito bites.

* * * * *